United States Patent
Mehta

(10) Patent No.: US 11,883,321 B2
(45) Date of Patent: Jan. 30, 2024

(54) HEATING DEVICE

(71) Applicant: PLEXAA LTD, London (GB)

(72) Inventor: Saahil Mehta, Los Angeles, CA (US)

(73) Assignee: PLEXAA LTD, London (GB)

(*) Notice: Subject to any disclaimer, the term of this patent is extended or adjusted under 35 U.S.C. 154(b) by 761 days.

(21) Appl. No.: 16/777,574

(22) Filed: Jan. 30, 2020

(65) Prior Publication Data

US 2020/0268550 A1 Aug. 27, 2020

(30) Foreign Application Priority Data

Jan. 31, 2019 (GB) .................................... 1901358

(51) Int. Cl.
| | |
|---|---|
| A61F 7/02 | (2006.01) |
| A61B 5/01 | (2006.01) |
| A61B 5/0295 | (2006.01) |
| A61B 8/06 | (2006.01) |
| A61F 7/00 | (2006.01) |

(52) U.S. Cl.
CPC .................. *A61F 7/02* (2013.01); *A61B 5/01* (2013.01); *A61B 5/0295* (2013.01); *A61B 8/06* (2013.01); *A61F 2007/0003* (2013.01); *A61F 2007/0021* (2013.01); *A61F 2007/0071* (2013.01); *A61F 2007/0093* (2013.01); *A61F 2007/0226* (2013.01); *A61F 2007/0234* (2013.01); *A61F 2007/0282* (2013.01)

(58) Field of Classification Search
CPC .............. A61F 7/007; A61F 2007/0071; A61F 2007/0073; A61F 2007/0074; A61F 2007/0075; A61F 2007/0234
See application file for complete search history.

(56) References Cited

U.S. PATENT DOCUMENTS

| | | | | |
|---|---|---|---|---|
| 5,050,595 | A | * | 9/1991 | Krafft ..................... A61F 7/007 450/55 |
| 9,131,883 | B2 | * | 9/2015 | Al-Ali ..................... A61B 5/021 |
| 9,339,412 | B2 | * | 5/2016 | Diller ........................ A61F 7/00 |

(Continued)

FOREIGN PATENT DOCUMENTS

| | | |
|---|---|---|
| JP | 2014171596 A | 9/2014 |
| WO | 01/28622 A2 | 4/2001 |

(Continued)

OTHER PUBLICATIONS

European Search Report in related application GB1901358.0 dated Jul. 2, 2019.

(Continued)

*Primary Examiner* — Kaitlyn E Smith
(74) *Attorney, Agent, or Firm* — Patterson + Sheridan, LLP

(57) ABSTRACT

A heating device is provided comprising: a wearable layer conformable to a part of a user's body; a heat source attached to the wearable layer for applying heat to a region of a user's body; a blood flow sensor attached to the wearable layer configured to detect a parameter indicative of blood flow in or adjacent to the region of the user's body and generate a signal indicative thereof; and one or both of: (i) a processor in electrical communication with the blood flow sensor for determining the blood flow in or adjacent to the region of the user's body based upon the signal; or (ii) a transmitter for transmitting the signal to a remote device.

13 Claims, 3 Drawing Sheets

(56) References Cited

U.S. PATENT DOCUMENTS

| 9,744,073 B2* | 8/2017 | Van Duren ........ A41D 13/1236 |
| 2005/0103353 A1 | 5/2005 | Grahn et al. |
| 2007/0060987 A1* | 3/2007 | Grahn ....................... A61F 7/02 |
| | | 607/104 |
| 2009/0107984 A1* | 4/2009 | Kohn ..................... A61F 7/007 |
| | | 219/528 |
| 2017/0157430 A1 | 6/2017 | Cheatham, III et al. |

FOREIGN PATENT DOCUMENTS

| WO | 2010/088914 A1 | 8/2010 | |
| WO | 2017/035341 A1 | 3/2017 | |
| WO | WO-2017035341 A1 * | 3/2017 | |
| WO | WO-2018102182 A1 * | 6/2018 | ............. A61F 7/007 |

OTHER PUBLICATIONS

European Search Report in related applicaiton EP 20154766 dated Nov. 20, 2020.
European Search Report in related application EP 23151741, dated Feb. 28, 2023.

* cited by examiner

HEATING DEVICE

CROSS-REFERENCE TO RELATED APPLICATIONS

This application claims benefit of the United Kingdom Patent Application No. 1901358.0, filed Jan. 31, 2019, the entire contents of which are incorporated herein by reference.

It is generally known to use heat to improve wound healing. Surgical-site complications are relatively common and up to 40% of patients worldwide experience problems with wound healing.

The advantages of this heat treatment may also be many types of surgeries such as abdominoplasties, mastectomy, vascular surgery, or wounds following sternotomy, laparotomy, complex free tissue reconstructions or other cosmetic procedures.

In a particular example, patients with breast cancer who undergo mastectomies and reconstructive breast surgery often have issues with skin necrosis. This can have significant effects upon wound healing and eventual scarring of the area. This skin necrosis can result in further operations being necessary which further extend a patient's hospital stay and ultimately result in an inferior cosmetic result. The extension to the hospital stay is both inconvenient for the patient and introduces further pressures on to the health system. Trials such as those in *Local Heat Pre-Conditioning in Skin Sparing Mastectomy; a Pilot Study* of Mehta et al., 2013 and *A randomised controlled feasibility trial to evaluate local heat preconditioning on wound healing after reconstructive breast surgery: the preHEAT trial* of Mehta et al., 2019 have shown how a pre-surgery heating regime using hot water bottles and thermometers can reduce the incidents of skin necrosis following mastectomy by as much as 24%.

Heat treatment can also help with the healing of chronic wounds. For example, venous leg ulcers can be healed at a faster rate with heat being applied.

A further particular example where heat application may improve results is following the removal of fat from elsewhere in a patient's body and injection into the face or breast for cosmetic procedures. This transferred fat achieves a more natural and permanent look but needs to establish a blood supply in order to survive. Typically, patients are over-corrected to allow for some of the fat which does not end up receiving a blood supply to be absorbed by the body. Heat pre-conditioning could improve the survival of fat in this region.

An example of known devices for providing a heat treatment is given in WO 2010/088923 A1. A fluid from a thermally insulated storage container is heated and pumped through a network of channels in a pad applied to a user's body for applying a heat to a user. The effect of the device is hard to monitor and must be carried out indirectly by observation. This results in an unreliable and slow system.

There is therefore a need for an improved device for these scenarios.

A heating device according to the present invention is provided according to claim 1. This provides an easy to use device which allows effective targeted heat to be applied to a region of a user's body and for the effects of the heating to be monitored to achieve better healing.

The heat source may be an electric heat source. This is easily controllable and provides an easily wearable device.

The heat source may be configured to maintain a first pre-set temperature of between 40° C. and 50° C.; and a second pre-set temperature of between 30° C. and 40° C. These two temperature ranges may be useful for pre- and post-operative heating.

The heating device may comprise a plurality of blood flow sensors configured to detect a parameter indicative of blood flow at different positions in or adjacent to the region of the user's body. This allows a more detailed and precise profile of blood flow to be derived. The plurality of blood flow sensors can be configured to be positioned on user's body at locations corresponding to the surgical site (and hence the wound healing site) as well as areas of the user's body not on the wound healing site.

The or each blood flow sensor may use at least one of plethysmography, acoustic or thermal sensing to detect the parameter indicative of blood flow. These are particularly suitable methods for devices of this size.

The heat source may be configured to apply a pulsatile heating pattern. Such a pattern is beneficial for certain application profiles.

The heating device may further comprise an additional sensor configured to detect the temperature of the region of a user's body. This allows the physical effect of the heating on the user to be determined in order to confirm the effectiveness and regulate temperature.

The wearable layer may comprise a flexible outer layer, a heating layer incorporating the heat source and an inner layer comprising the sensor(s). Such an arrangement provides a flexible, comfortable device. Such a device may more readily conform to parts of the user's body which should receive the heat, for example to the user's breast.

The heating device may be a bandage, face mask or bra cup, or an insert for inserting into a bandage, face mask or bra cup. These devices would particularly benefit from the heat application.

The heating device may be a bra cup or an insert for inserting into a bra cup, and the heating device and blood flow sensor(s) may be arranged to generally surround, in use, a user's areola. This arrangement is useful for heating before and after breast surgery, such as breast reconstruction.

The heating device may comprise a plurality of blood flow sensors arranged in one or more circles generally centred, in use, on a user's areola. This allows blood flow into and out of the breast to be easily and accurately monitored. The innermost circle of blood flow sensors may be arranged to generally align with the outer area of the user's areola. The plurality of blood flow sensors in each circle may be distributed in rotational symmetry.

The blood flow sensor(s) may comprise a first blood flow sensor configured to detect blood flow in a skin flap region and a second blood flow sensor configured to detect blood flow in a free flap region. This allows separate monitoring of the two separate regions, which may have different parameters to monitor. The first flow blood sensor may be configured to detect a parameter to be monitored and the second blood flow sensor may be configured to detect a reference blood flow. The signal from the first blood flow sensor may be compared to signal from the the second blood flow sensor. This may illustrate the difference between blood flow in the skin flap region and the free flap region.

A system is provided according to claim 13. This system exhibits the benefits discussed above.

The processor may be a further processor within a remote device in communication with the transmitter (ii). This can allow a user's healthcare professional to receive a notification or alert when the blood flow is not large enough. Additionally, or alternatively, the user can receive an alert or notification when the blood flow is not large enough. The user can then be brought in for further treatment as necessary. Additionally, or alternatively, the user can reposition the heating device if necessary.

A method of heating a region of a user's body is provided according to claim 15. This method provides the benefits discussed above.

The activation of the heat source may be cyclical. Such a pattern is beneficial for certain application profiles. Further heat source profiles can also be used that are suitable for improving wound healing.

The method may be carried out a period of time before surgery, preferably 12 hours. This can improve the outcome for patients after the surgery.

The controller may be configured to maintain the temperature of the heat source to between 40° C. and 50° C. These temperatures have been shown to be particularly effective before surgery.

The activation of the heat source may be generally constant to output a constant temperature. This may be particularly beneficial in certain uses.

The method may be carried out after surgery. This can improve the outcome for patients after the surgery.

The heating device may be configured to maintain the temperature of the heat source to between 30° C. and 40° C. These temperatures have been shown to be particularly effective after surgery.

The heat improves the blood supply to the healing tissue which then aids in the healing process. This is particularly relevant in relation to the healing of skin as this is an "end-organ" which requires optimal blood flow to heal without complication.

The present invention will be described, by way of example only, with reference to the accompanying figures in which.

Figure 1:
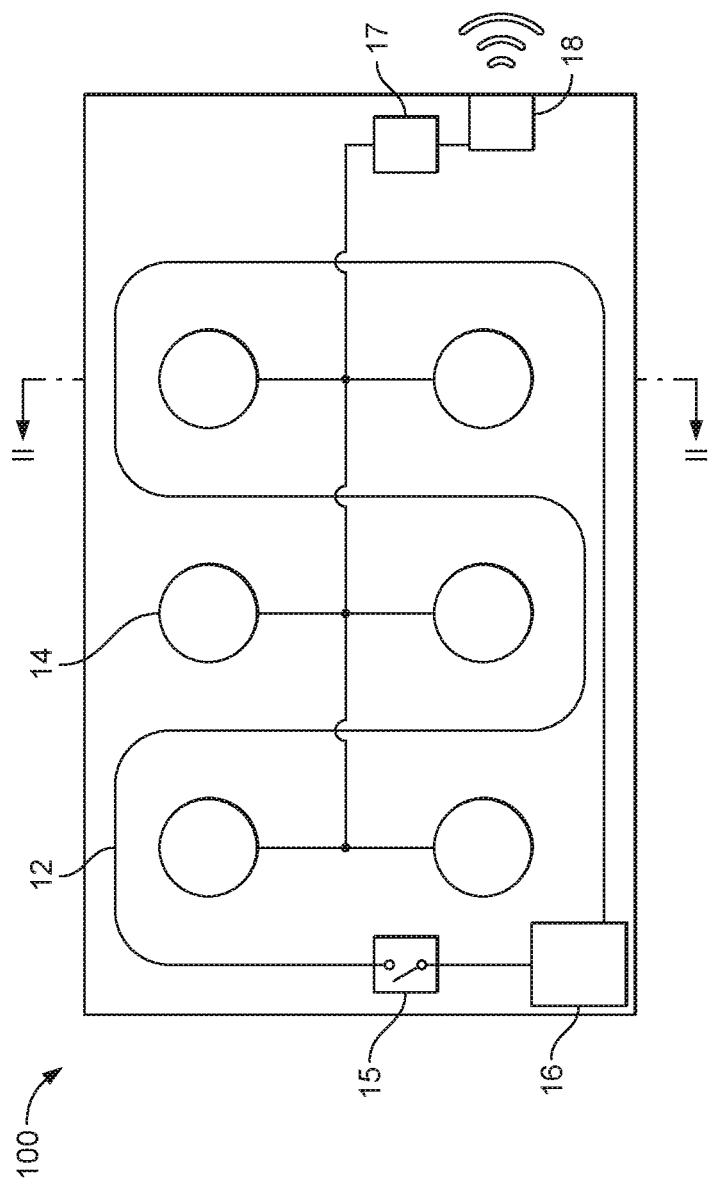
FIG. 1 shows a heating device and system according to the present invention.
Figure 1:
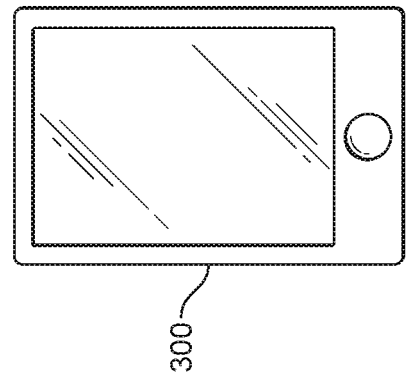

FIG. 1 shows a heating device 100 according to the present invention. The heating device 100 comprises a heat source 12 for generating heat. The heat source 12 is attached to or forms a part of a wearable layer conforming to a region of a user's body. When, in use, the heating device 100 is applied to a region of a user's body, the heat generated by the heat source 12 is transferred from the heating device 100 to the user. The heating device 100 may comprise multiple heat sources 12 for generating heat. Additionally, or alternatively, the heating source 12 may further comprise multiple heating elements for generating heat. The transfer of heat from the heat source 12 to the user is suitable for and arranged to increase the blood flow of the user in the region being heated.

In the embodiment of FIG. 1 the heat source 12 is an electric heat source, in particular, an electric resistance heat source. That is, the heat source 12 generates electricity by passing a current through a resistive wire. To this end, a battery 16 is provided in connection with the heat source 12. The heat source 12 may be suitable for providing a generally constant level of heat. This may be via a control loop with sensors, or any other known method.

A switching means 15 is provided for activating and deactivating the generation of heat within the source. The switching means 15 may be manually activated. Alternatively, or in addition, the switching means may be periodically activated by a processor or other timing circuit to deliver a cyclical or timed output of heat from the heat source 12. Such a heating profile may also be described as periodic.

The heating device 100 further comprises one or more sensors 14 configured to detect blood flow in or adjacent to the region of the user's body being heated. While these sensors 14 may directly generate an electrical signal indicative of the blood flow, it is also anticipated that the sensors 14 may generate a signal indicative of a parameter indicative of blood flow. This signal can then be processed by a processor 17 in communication with the sensors 14 to convert the parameter into blood flow. The processor 17 may be a separate component or may be integrated into the sensors 14. For example, the sensors 14 may directly measure temperature and derive the blood flow from this measurement.

The sensors 14 configured to detect blood flow can do so via any known method for determining blood flow. In particular, this may include one or more of plethysmography, photo-plesmography, laser Doppler flowmetry, laser speckle contrast imaging, acoustic or thermal sensing or any other suitable method. Exemplary sensors are disclosed in *Epidermal devices for noninvasive, precise, and continuous mapping of macrovascular and microvascular blood flow* to Webb et al., 2015. The sensors 14 of Webb et al. comprise a local heat source separate to the main heat source 12, transmission of the local heat is detected as set out in the paper. This local heat source can effectively be superimposed upon the global heating of the main heat source 12. That is, the local heat source heats to a greater temperature than the main heat source 12.

Alternatively, the main heat source 12 may take the place of the local heat sources of Webb et al. In this case, the sensors may generally surround the main heat source 12. In effect, this produces a large version of the sensor disclosed in Webb et al.

Further alternatively, the local heat source of the sensor(s) may form the main heat source 12. This is particularly relevant for an embodiment with multiple sensors where the local heat sources can collectively form the main heat source 12.

It is anticipated that any of these arrangements may be combined to include multiple arrangements of sensors.

In particular embodiments, where the main heat source 12 is being used in a cyclical pattern (a period of heating followed by a period of inactivity) the sensors 14 of Webb et al. may only operate during the period of inactivity of the main heat source 12.

As discussed above, the application of heat to the region of the user's body encourages blood flow to this region. A lower threshold of blood flow is set at a level which is understood to improve the recovery of skin in the area. The sensors 14 detect the blood flow and allow comparison with this threshold to confirm that an improved blood flow is being achieved in the region.

The sensors 14 may further be in communication with a transmitting device 18 for communicating with a remote device 300. The sensors 14 may also be in communication either with a further processor, either locally provided or provided on the remote device. This further processor, and/or the processor 17 may be configured to compare the blood flow to a threshold value. If the signals fall below the threshold value the processor 17 may generate a notification for the user. The notification may be in any suitable form including, but not limited to, auditory, visible, or digital such as a record stored within a database or an alert on a user's mobile device.

The transmitter 18 may transmit the signals from the sensors 14 or processed information thereof from the processor 17. In certain embodiments, there is no processor 17 and the raw signals from the sensors 14 can be transmitted by the transmitter 18. The transmitter 18 communicates with a remote user device 300. In particular, the remote user device 300 may be a device accessible by the user and/or a medical professional, such as a smart phone. The remote user device 300 may comprise its own processor which is able to compare the blood flow to the threshold value in order to generate the notification. The communication between the remote device 300 and the transmitter 18 may be via any known wired or wireless method. In particular, the communication may be via the Bluetooth protocol. The transmission of the data to the remote device 300 allows either the user or the user's medical professional to review the effectiveness of the heating profile being applied to the user. That is, to ensure that the heating profile is acting as intended and there is an increased blood flow in the regions of the user's body which are being heated.

The remote device 300 may alternatively, or additionally, comprise a "cloud" sever remote from the heating device 100. This allows the data generated by the device 100 to be remotely accessed by both the user and the healthcare professional. Alternatively, the remote device 300 may itself further comprise a transmitter which transmits the data to this remote server.

A medical professional reviewing the data can quickly see whether any regions are not receiving satisfactory blood flow and, as necessary, instruct the patient to alter their routine or come in for a further health check-up. This allows live monitoring of the process and hence better outcomes.

The heating device 100 of FIG. 1 is generally in the form of a bandage or strap, but the technology can be used for any suitable device. For example, the heating device 100 may be a bandage, face mask or bra cup, or an insert for inserting into a bandage, face mask or bra cup. The heating device 100 may be shaped or have its components arranged so as to be specifically adapted for a particular usage. For example, the heat source 12 and/or sensors 14 may be only provided in particular regions of the device 100 which correspond to treatment areas. For example, a bandage or face mask could be configured to generally heat a user's ear region for ear surgery applications.

Figure 2:
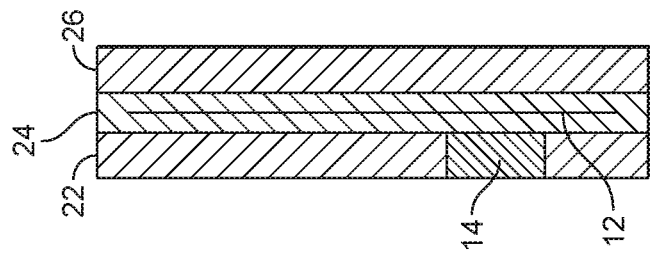
FIG. 2 shows a side view of the heating device of FIG. 1.

FIG. 2 shows a side view of the heating device of heating device 100 of FIG. 1 along the line II. As can be seen in FIG. 2, the heating device 100 is generally formed of a tri-laminate structure. That is, an inner layer 22 in which the sensors 14 are embedded or attached, a mid heating layer 24 with the source of heat 12 and an outer flexible layer 26. These layers form the wearable layer which conforms to a region of a user's body. Preferably, the inner layer 22 may be cushioned and/or insulated in order to increase the comfort of the device 100 as well as its ability to retain heat within the body of the user. In normal use, the inner layer 22 will contact the user's body. Suitable materials for such an inner layer include wool and other natural heat materials. Typical materials for the outer layer include lycra. The materials for the layers may be selected to compliment the source of heat chosen.

While in the example of FIGS. 1 and 2 the battery 16, processor 17 and transmitter 18 are generally provided on the same portion of the heating device 100 as the source of heat 12, this is not necessarily the case. In particular, in certain other embodiments these components may be provided in a distally attached component. This component may be attachable and detachable from the rest of the heating device 100 in order to ensure greater portability and comfort. This also can allow the component to be removed when cleaning the heating device 100.

Figure 3:
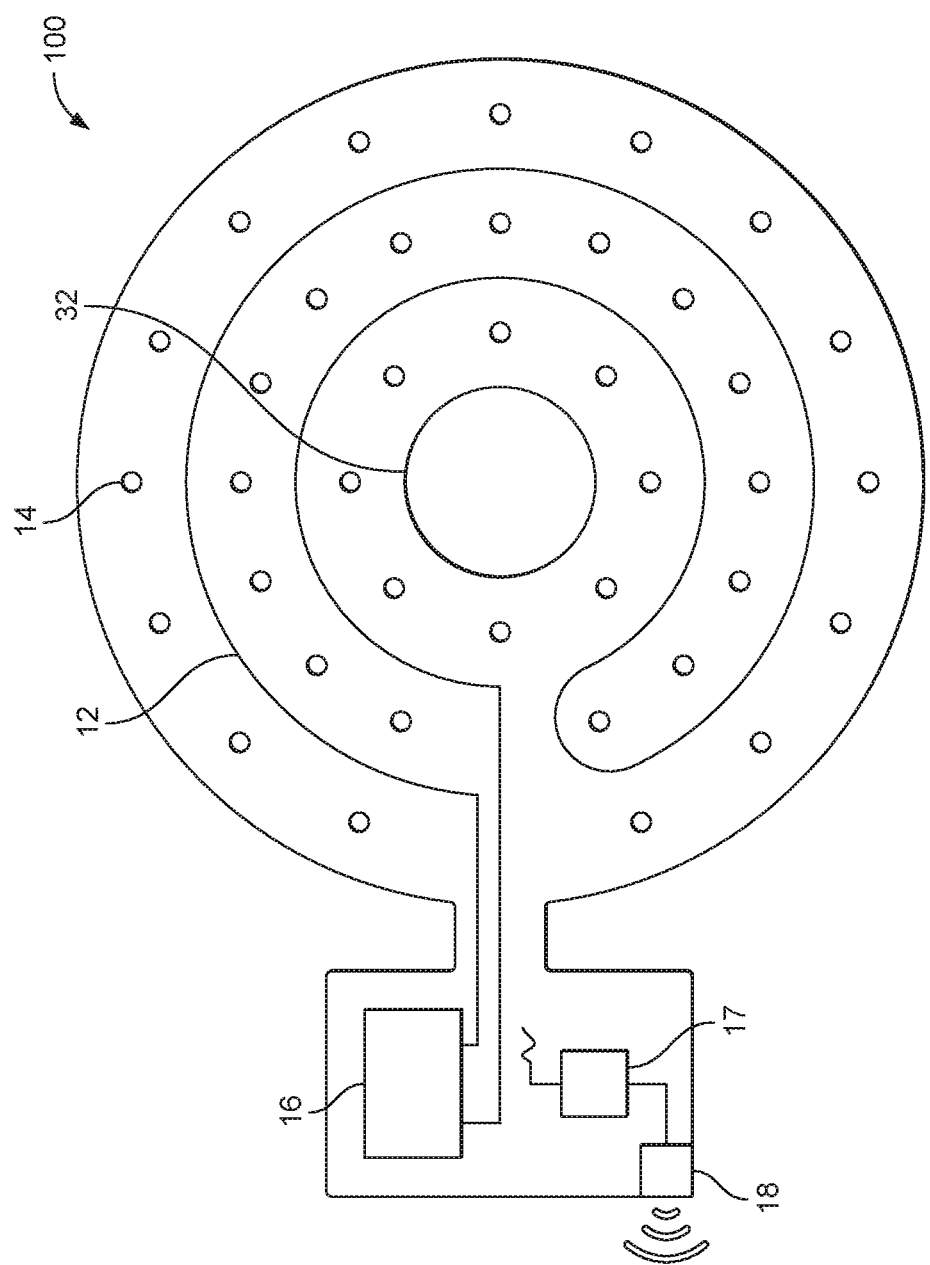
FIG. 3 shows a schematic view of a further heating device according to the present invention.

FIG. 3 depicts a particular embodiment of a heating device 100 suited for use with mastectomy patients. The heating device 100 is generally in the form of a bra cup or insert therefore. By that, it is intended that the major part of the heating device 100 is generally circular and receives the user's breast. While the heating device 100 may be a single cup (i.e. intended to receive a single breast) it is also anticipated that a dual cup design for the heating device more similar to a traditional bra may be used.

The heating device 100 is generally similar to the device 100 of FIG. 1. The heat source comprises circumferentially arranged resistive wires 12 and the sensors 14 are arranged in an array of generally concentric circles. As shown in this embodiment, the battery 16 processor 17 and transmitter 18 are provided separate to the actual cup of the heating device 100. The heating device 100 may comprise attachment means for attaching to the user's breast or may be arranged to be inserted into a conventional bra of the user. For ease of viewing, the wiring for the sensors 14 has been omitted from FIG. 3.

The heating device 100 may generally comprise an inner region 32 and an outer region. The inner region 32 may be configured in use, to generally align with the user's areola and nipple.

The heat source 12 and sensors 14 may or may not extend into this central region 32. In embodiments where the heat source 12 does extend into the central region 32 it may be modified in this region to deliver suitable heat for these areas of the user's body. Likewise, the sensors 14 may be modified in this region to detect blood flow in this region specifically.

The heating device 100 of FIG. 3 likewise may comprise the generally tri-laminate structure of FIG. 2. This is particularly important as the comfort and durability of the device is important in this environment.

During breast reconstruction surgery, skin and fat tissue is generally taken from an abdominal region of a patient. This skin and fat tissue is generally referred to as a "flap" as it comprises its own blood supply (i.e. veins and arteries). Commonly, it is referred to as a "free flap" once it is detached from the abdominal area. The tissue in the patient's breast area which is not removed is referred to as the "mastectomy skin flap".

This free flap is inserted into the patient's breast through the areola region (the areola and nipple having previously been removed, along with internal breast tissue and fat) to form the reconstructed breast. The epidermal layers of the free flap are removed, except for the region of the flap which aligns with the insertion area. This region will form the patient's replacement areola and nipple. The blood flow passageways of the free flap are connected to the existing passageways in the breast.

In particular embodiments, the sensors 14 of the heating device 100 of FIG. 3 may comprise at least one first sensor 14A for sensing skin flap health and at least one second sensor 14B for sensing free flap health. The second sensor 14B for sensing free flap health is able to specifically determine how the transferred flap is behaving. If the sensor 14B detects insufficient blood flow, an alert may be generated for the user or the user's medical professional. The sensor 14B may be a different type of sensor to the sensor 14A to allow it to specifically target the free flap blood flow.

Alternatively, or additionally, the sensor 14B may locally heat to a different temperature compared to the sensor 14A (if both sensors are according to Webb et al.) Alternatively, or additionally, the signals from the sensor may be filtered to focus upon the free flap blood flow. In particular, free flap blood flow may be generally more pulsatile than blood flow in the skin flap. The heating device 100 or remote device 300 may be arranged to filter the raw signal from the sensor 14B in order to identify this pulsatile signal.

A method of using the heating device 100 is provided before and after a surgery. In particular, this is relevant where the surgery is a breast surgery such as mastectomy.

Before the surgery, the heating device 100 is applied to the user's body and the heat source is activated to apply heat to the user's body in the region of the heating device 100. The application of heat may be in a pulsatile manner. This heat causes enhanced blood flow. That is, the heat may be applied in periods of high temperature heating and periods of low temperature heating. The period of low temperature heating may have a zero or negligible output from the heat source 12, or may be generally set at a comfortable body temperature. For example, the application of heat may come in periods of activity and inactivity of the heat source 12. For example, the heat source 12 may be active, or in a period of high temperature heating, for 30 minutes, followed by inactivity, or a period of low temperature heating, for 30 minutes, followed by activity, or a period of high temperature heating for 30 minutes and so forth.

Such a heating profile has been shown to be particularly useful in patients before surgery takes place. This heating profile may be applied for a period of time such as 12 hours before the surgery. The device may be configured to heat the region of the user's body to between 40° C. and 50° C. during this time, preferably, to 43° C. The sensors 14 provided in the heating device 100 are able to detect the blood flow in the region of the user's body and process and/or transmit this data. This allows the data to be reviewed by the user and/or the user's medical professional in order to ensure that the device is operated as intended. This allows the user and/or medical professional to have confidence in the desired results of the device.

In the post-operation method a generally constant heat may be provided by the heating device 100. In particular, the heating device 100 may be configured to heat the region of the user's body to between 30° C. and 40° C., preferably to between 36° C. to 38° C. Again, studies have shown that this is an optimal temperature to heat the region of the user's body after surgery in order to have the best post-operation outcomes. This post-operative heating may be to a substantially constant temperature.

As noted above, these methods are particularly applicable with the heating device 100 of FIG. 3 which is generally used for breast surgery such as mastectomies. However, these methods, or variations thereupon, may be used in any scenario where benefit is shown for a patient.

Figure 4:
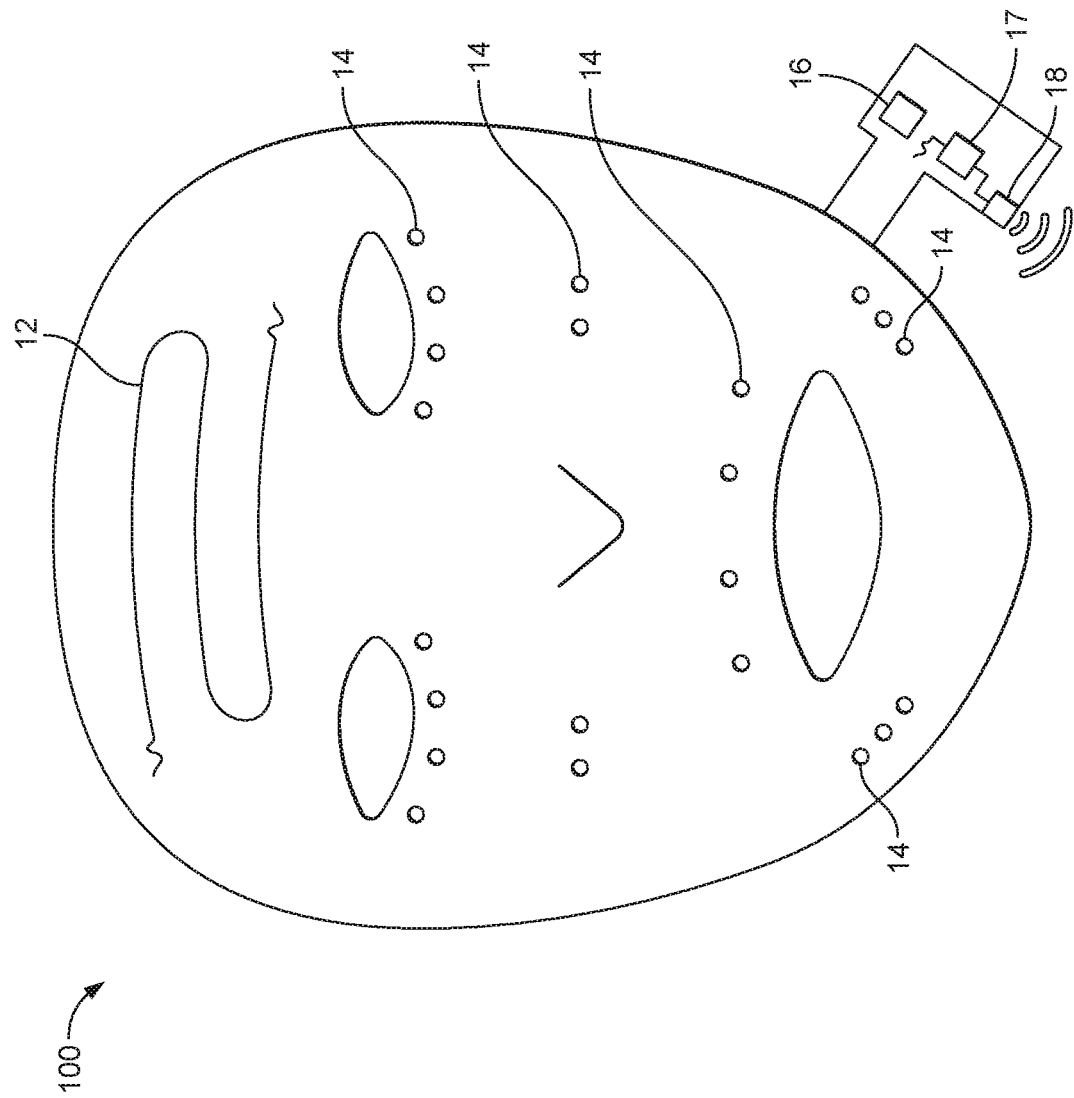
FIG. 4 shows a schematic view of a further heating device according to the present invention.

FIG. 4 shows a further particular embodiment of a heating device 100, particularly suitable for use on a face. The heating device 100 is generally similar to the previously described devices. The heat source 12 may be provided generally across the entire inner surface of the device 100. Alternatively, the heat source 12 may only be located in particular regions of interest. In certain embodiments the heat source 12 is selectively powered such that individual regions of the device 100 can be heated while other regions are not.

The sensors 14 may generally be provided in specific regions where improved blood flow may be beneficial. For example, this may be in or around one or more of the: lower eyelid sulcus, nasolabial folds, upper or lower lips, temporal region, jowl area, and/or malar region.

Again, the wiring for the sensors 14 has been omitted from the Figure for clarity. The data generated by the sensors 14 is generally handled and processed as discussed above with respect to the other embodiments.

The invention claimed is:

1. A heating device for wound healing, the heating device comprising:
   a wearable layer conformable to a part of a user's body;
   a heat source attached to the wearable layer for applying heat to a region of a user's body;
   one or more blood flow sensors attached to the wearable layer configured to detect a parameter indicative of blood flow in or adjacent to the region of the user's body and generate a signal indicative thereof; and
   one or both of:
      (i) a processor in electrical communication with the one or more blood flow sensors for determining the blood flow in or adjacent to the region of the user's body based upon the signal; or
      (ii) a transmitter for transmitting the signal to a remote device,
   wherein the heating device is a bra cup, or an insert for inserting into a bra cup, and the heating device and one or more blood flow sensors are arranged to generally surround, in use, a user's areola.

2. The heating device of claim 1, wherein the heat source is an electric heat source.

3. The heating device of claim 1, wherein the heat source is configured to maintain a first pre-set temperature of between 40° C. and 50° C.; and a second pre-set temperature of between 30° C. and 40° C.

4. The heating device of claim 1, comprising a plurality of blood flow sensors configured to detect a parameter indicative of blood flow at different positions in or adjacent to the region of the user's body.

5. The heating device of claim 1, wherein the one or more blood flow sensors use at least one of plethysmography, acoustic or thermal sensing to detect the parameter indicative of blood flow.

6. The heating device of claim 1, wherein the heat source is configured to apply a pulsatile heating pattern.

7. The heating device of claim 1, further comprising an additional sensor configured to detect the temperature of the region of a user's body.

8. The heating device of claim 1, wherein the wearable layer comprises a flexible outer layer, a heating layer incorporating the heat source and an inner layer comprising the one or more sensors.

9. The heating device of claim 1, comprising a plurality of blood flow sensors arranged in one or more circles generally centered, in use, on a user's areola.

10. The heating device of claim 1, wherein the blood flow sensor(s) comprise a first blood flow sensor configured to detect blood flow in a skin flap region and a second blood flow sensor configured to detect blood flow in a free flap region.

11. A system comprising:
a heating device for wound healing, the heating device having:
  a wearable layer conformable to a part of a user's body;
  a heat source attached to the wearable layer for applying heat to a region of a user's body;
  one or more blood flow sensors attached to the wearable layer configured to detect a parameter indicative of blood flow in or adjacent to the region of the user's body and generate a signal indicative thereof; and
  one or both of:
    (i) a processor in electrical communication with the one or more blood flow sensors for determining the blood flow in or adjacent to the region of the user's body based upon the signal; or
    (ii) a transmitter for transmitting the signal to a remote device,
  wherein the heating device is a bra cup, or an insert for inserting into a bra cup, and the heating device and the one or more blood flow sensors are arranged to generally surround, in use, a user's areola,
wherein either:
  the processor (i); or
  a separate processor in communication with the one or more blood flow sensors, is configured to compare the blood flow to a threshold value and generate a notification if the blood flow is less than the threshold value.

12. The system of claim 11, wherein the processor or the separate processor is within a remote device in communication with the transmitter (ii).

13. A method of heating a region of a user's body comprising the steps of:
providing a heating device, the heating device comprising:
  a wearable layer conformable to a part of a user's body;
  a heat source attached to the wearable layer for applying heat to a region of a user's body;
  one or more blood flow sensors attached to the wearable layer configured to detect a parameter indicative of blood flow in or adjacent to the region of the user's body and generate a signal indicative thereof; and
  one or both of:
    (i) a processor in electrical communication with the one or more blood flow sensors for determining the blood flow in or adjacent to the region of the user's body based upon the signal; or
    (ii) a transmitter for transmitting the signal to a remote device, wherein the heating device is a bra cup, or an insert for inserting into a bra cup, and the heating device and the one or more blood flow sensors are arranged to generally surround, in use, a user's areola;
placing the wearable layer on a user's body so that the heating device is in thermal contact with a user's body;
activating the heat source to apply heat to a region of the user's body; and
using the blood flow sensors to detect blood flow in the region of the user's body.

* * * * *